United States Patent
Glauner et al.

(10) Patent No.: US 8,322,195 B2
(45) Date of Patent: Dec. 4, 2012

(54) APPARATUS AND METHOD FOR MEASURING THE COAGULATION CHARACTERISTICS OF A TEST LIQUID

(75) Inventors: Martin Glauner, Grenzach-wyhlen (DE); Axel Schubert, Munich (DE); Max Kessler, Munich (DE)

(73) Assignee: C A Casyso AG, Muttenz (CH)

( * ) Notice: Subject to any disclaimer, the term of this patent is extended or adjusted under 35 U.S.C. 154(b) by 583 days.

(21) Appl. No.: 12/520,034

(22) PCT Filed: Dec. 18, 2007

(86) PCT No.: PCT/IB2007/003966
§ 371 (c)(1),
(2), (4) Date: Feb. 26, 2010

(87) PCT Pub. No.: WO2008/075181
PCT Pub. Date: Jun. 26, 2008

(65) Prior Publication Data
US 2010/0170327 A1    Jul. 8, 2010

(30) Foreign Application Priority Data
Dec. 19, 2006    (GB) .................................. 0625393.4

(51) Int. Cl.
*G01N 11/14*    (2006.01)
*G01N 37/00*    (2006.01)

(52) U.S. Cl. ...................................... 73/54.33; 73/64.41

(58) Field of Classification Search .................. 73/54.26, 73/54.27, 54.32, 54.33, 54.34, 64.41, 64.42
See application file for complete search history.

(56) References Cited

U.S. PATENT DOCUMENTS

| | | | | |
|---|---|---|---|---|
| 2,796,758 | A * | 6/1957 | Myers et al. | 73/54.32 |
| 3,053,078 | A * | 9/1962 | Jewett | 73/53.01 |
| 4,343,190 | A * | 8/1982 | Danko et al. | 73/846 |
| 4,352,287 | A * | 10/1982 | Orth et al. | 73/54.39 |
| 6,591,664 | B2 * | 7/2003 | Litton | 73/54.41 |
| 2002/0110554 | A1 | 8/2002 | Lewis et al. | |
| 2003/0154772 | A1* | 8/2003 | Jackson | 73/54.28 |
| 2006/0177811 | A1 | 8/2006 | Sehgal et al. | |
| 2008/0034844 | A1* | 2/2008 | Manneville | 73/54.23 |

FOREIGN PATENT DOCUMENTS

| | | |
|---|---|---|
| EP | 1 627 725 | 2/2006 |
| WO | 88/00956 A1 | 2/1988 |
| WO | WO 2005043131 A1 * | 5/2005 |

OTHER PUBLICATIONS

Luddington R J: "Thrombelastography/thromboelastometry." in Clinical and Laboratory Haematology Apr. 2005, vol. 27, No. 2, Apr. 2005, pp. 81-90.

* cited by examiner

*Primary Examiner* — Hezron E Williams
*Assistant Examiner* — Nathaniel Kolb
(74) *Attorney, Agent, or Firm* — Joyce von Natzmer; Agris & von Natzmer LLP

(57) ABSTRACT

An apparatus and a method for measuring the coagulation characteristics of a test liquid (1), in particular of a blood sample, is provided. According to the present invention standardized geometrical dimensions of a cup (2) and a respective pin (3) are modified for receiving maximum elasticity signal per volume test liquid without resulting in irreversible inelastic effects. In particular, the test liquid gap (8) between the cup (2) and the pin (3) is reduced, the diameter of the cup (2) and the pin (3) are increased and/or the geometry of test liquid accommodating portions (7; 10; 10') are optimized for increasing the ratio between signal amplitude and a needed amount of test liquid (1) compared to standardized equipment.

19 Claims, 5 Drawing Sheets

APPARATUS AND METHOD FOR MEASURING THE COAGULATION CHARACTERISTICS OF A TEST LIQUID

This is the U.S. national stage of International application PCT/IB2007/003966, filed Dec. 18, 2007 designating the United States, which claims priority to GB 0625393.4, filed Dec. 19, 2006, both of which are incorporated herein by reference in their entirety.

FIELD OF THE INVENTION

The present invention relates to an apparatus and a method for measuring the coagulation characteristics of a test liquid, in particular of a blood sample.

BACKGROUND

It is essential for survival that a wound stops bleeding, i.e. that the body possesses an adequate mechanism for haemostasis. The process of blood clotting can be activated in the case of injuries or inflammations by either extrinsic or intrinsic factors, e.g. tissue factor (TF) or Hagemann factor (F XII), respectively. Both activation channels are continued in a common branch of the cascade resulting in thrombin formation. The thrombin itself finally initiates the formation of fibrin fibres which represent the protein backbone of blood clots.

The other main constituent of the final blood clot are the thrombocytes which are interconnected by the fibrin fibres and undergo a number of physiological changes during the process of coagulation. Within limits a lack of thrombocytes can be substituted by an increased amount of fibrin or vice versa. This is reflected in the observation that the thrombocyte counts as well as the fibrinogen concentration varies even within healthy patients.

Various methods have been introduced to assess the potential of blood to form an adequate clot and to determine the blood clots stability. Common laboratory tests such as thrombocyte counts or the determination of fibrin concentration provide information on whether the tested component is available in sufficient amount but lack in answering the question whether the tested component works properly under physiological conditions (e.g. the activity of fibrinogen under physiological conditions can not be accessed by common spectroscopic methods). Other common tests such as the prothrombin time (Quicktest) or the partial thromboplastin time (PTT) work on blood-plasma exclusively and therefore require an additional step for preparation and additional time which is unfavourable especially under POC (point of care) conditions.

Another group of tests which overcomes these problems is summarized by the term "viscoelastic methods". The common feature of these methods is that the blood clot firmness (or other parameters dependent there on) is continuously determined, from the formation of the first fibrin fibres until the dissolution of the blood clot by fibrinolysis. Blood clot firmness is a functional parameter, which is important for haemostasis in vivo, as a clot must resist blood pressure and shear stress at the site of vascular injury. Clot firmness results from multiple interlinked processes: coagulation activation, thrombin formation, fibrin formation and polymerization, platelet activation and fibrin-platelet interaction and can be compromised by fibrinolysis. Thus, by the use of viscoelastic monitoring all these mechanisms of the coagulation system can be assessed.

A common feature of all these methods used for coagulation diagnosis is that the blood clot is placed in the space between a cylindrical pin and an axially symmetric cup and the ability of the blood clot to couple those two bodies is determined.

The first viscoelastic method was called "thrombelastography" (Hartert H: Blutgerinnungsstudien mit der Thrombelastographie, einem neuen Untersuchungsverfahren. Klin Wochenschrift 26:577-583, 1948). In the thromboelastography, the sample is placed in a cup that is periodically rotated to the left and to the right by about 5°, respectively. A pin is freely suspended by a torsion wire. When a clot is formed it starts to transfer the movement of the cup to the pin against the reverse momentum of the torsion wire. The movement of the pin as a measure for the clot firmness is continuously recorded and plotted against time. For historical reasons the firmness is given in millimeters.

The outcome of a typical measurement of this kind is illustrated in FIG. 1. One of the most important parameters is the time between the chemically induced start of the coagulation cascade and the time until the first long fibrin fibres have been build up which is indicated by the firmness signal exceeding a defined value. This parameter will be called clotting time or just CT in the following. Another important parameter is the clot formation time (CFT) which gives a measure for the velocity of the development of a clot. The CFT is defined as the time it takes for the clot firmness to increase from 4 to 20 mm. The maximum firmness a clot reaches during a measurement, further on referred to as maximum clot firmness or just MCF, is also of great diagnostic importance.

Modifications of the original thromboelastography technique (nowadays also called thromboelastometry) have been described by Cavallari et al. (U.S. Pat. No. 4,193,293), by Do et al. (U.S. Pat. No. 4,148,216), by Cohen (U.S. Pat. No. 6,537,819), by Hartert et al. (U.S. Pat. No. 3,714,815) and by Calatzis et al. (U.S. Pat. No. 5,777,215).

During coagulation the fibrin backbone creates a mechanical elastic linkage between the surfaces of the blood-containing cup and a pin plunged therein. A proceeding coagulation process induced by adding one or more activating factor(s) can thus be observed. In this way, various deficiencies of a patient's haemostatic status can be revealed and used for proper medical intervention.

A general advantage of thromboelastometry compared to other laboratory methods in this field therefore is that the coagulation process and the change of mechanical properties of the sample are monitored as a whole. This means that contrary to the other laboratory methods mentioned above, thromboelastometry does not only indicate if all components of the coagulation pathways are available in sufficient amounts but also if each component works properly.

To get detailed information on the correct amount and function of the thrombocytes as well as the fibrinogen and certain factors nowadays there is an increasing amount of chemicals available which activate or inhibit certain components of the coagulation system. This allows determining exactly at which point of the coagulation system a problem is located.

For practical reasons these chemicals are usually injected to the disposable plastic cup which later on is used for the measurement by using a pipette (either a manual or an automatic one). In the last preparation step, after the blood of plasma sample has been added, the whole amount of sample (blood/plasma and the additional chemicals) is mixed by drawing it into the pipette tip and dispensing it into the cup again.

The possibility to chemically activate or to disable certain components of the coagulation system is especially useful in conjunction with state-of-the-art thromboelastometers such as the ROTEM (Pentapharm GmbH, Munich, Germany) which allows conducting four measurements in parallel. This allows to achieve detailed information on the current status of the coagulation-situation of a patient and therefore allows an appropriate therapy within several minutes. Furthermore, the efficiency of a certain medication might be tested in vitro prior to the application to the patient.

This is of particular importance in case of patients struck by massive blood loss as it often occurs in context with multiple traumata. The blood of such patients often is diluted due to infusions which are administered to replace the loss in volume. This leads to a decrease of the concentration of thrombocytes as well as coagulation factors such as fibrinogen.

A topic of outstanding importance in this context is the determination of the fibrin networks contribution to the final stability of a growing blood clot. This can be achieved by adding a thrombocyte inhibitor, e.g. Cytochalisch D, to the sample before measurement. That way the activity of fibrin becomes directly accessible.

One problem in thromboelastometric measurements may result from decreasing signal to noise ratio if the total firmness of the sample becomes comparably low. This situation especially occurs for measurements in which the thrombocytes are chemically inactivated (such as mentioned above) because these tests naturally exhibit a low final firmness. The situation becomes even worse if the original blood sample is highly diluted due to the earlier addition of substitutes. Since a sufficient signal to noise ratio might be crucial for an appropriate fibrinogen medication (in particular to choose an appropriate amount of fibrinogen substitute) it would be an important achievement to increase the sensitivity of those tests.

The reason for the rather low signal to noise ratio when testing the fibrinogen function of pathologic samples originates from applying the thromboelastometric method near the lower limit of sensitivity: The geometry of the standardized disposables (the outer diameter of the pin is about 5.0 mm and the space between cup and pin is about 1.0 mm) and the amount of blood used per test were originally chosen to obtain best signals when measuring conventionally activated 'full' clots of non-pathologic blood samples. Such tests result in values for the maximum clot firmness (MCF) between 50 and 70 mm, which is the most sensitively detected range of the method. In thrombocyte inhibited tests, however, only the fibrinogen contribution to the clot is measured, since the platelet functionality is completely suppressed. Hence, these tests yield only MCF's between 15 and 25 mm for normal patients, while MCF's well below 10 mm are typically observed in the case of pathologic samples—with no definable lower limit. Considering a general sensitivity level of about 2 mm for the current disposable geometry, higher test-to-test result variations (coefficient of variations) are a consequence when measuring such samples.

The magnitude of the measured signal is proportional to the torque being transmitted to the shaft of the instrument by elastic fibrin fibres between cup and pin walls. Therefore it depends on the thickness of the blood clot on the total area of the clot surface.

As a conventional solution, the measurement signal could be increased by increasing the sample amount if the expected clot firmness is rather low. However, this approach limited to the amount of blood usually available for coagulation analysis in clinical practice. A further practical limitation of this approach is that the maximum increase of sample volume and cup is limited due to the geometric dimensions of the commercially available thromboelastometers. Furthermore, there are situations where the amount of blood available for analysis is further limited, especially in surgery on infants (due to ethical considerations) or in pharmaceutical industry where mice are used as donors. Beyond that, thromboelastography in the pharmaceutical industry for drug development has an increased demand for extremely high accuracy measurements on small samples.

To reach maximum accuracy, it is desirable to achieve that the transfer of torque to the instrument shaft is shifted to the most sensitive range of the instrument for each test.

The purpose of this invention is to achieve this by optimization of the geometry of cups and/or pins intended for tests with currently low signal amplitudes. Another field of application would be the pharmacological industry or any situation where the available amount of sample is limited.

It is therefore an object of the present invention to provide an apparatus for measuring the coagulation characteristics of a test liquid, whereby the ratio between signal amplitude and the needed amount of test liquid is increased. It is also an object of the invention to provide a method for measuring the coagulation characteristics of a test liquid by means of such an apparatus.

The object is attained by an apparatus comprising the features disclose herein, in particular an apparatus comprising measuring coagulation characteristics of a test liquid, in particular of a blood sample, comprising: a cup for receiving said test liquid; a pin having a head portion suitable to be immersed into said test liquid of said cup; wherein said cup comprises at least one test liquid duct portion; wherein said head portion of said pin comprises at least one test liquid contacting portion, wherein each test liquid contacting portion is associated to and placeable inside the respective test liquid duct portion of said cup such that the lateral surfaces of the respective test liquid contacting portion of said pin and side walls of the associated test liquid duct portion of said cup are forming a test liquid gap there between having a predetermined width; and wherein said at least one test liquid duct portion and said associated test liquid contacting portion are shaped as a ring-segment, a method for measuring the coagulation characteristics of a test illiquid in particular a blood sample, via such an apparatus comprising: (a) measuring oscillation movement signal values by using said cup and said pin having predetermined geometrical dimensions; and (b) determining the coagulation characteristics of the test liquid using said signal values and a data carrier comprising a non-transient computer-readable medium containing code for executing this method.

Depending on the practical situation the present invention can be used either to increase the signal/noise ratio especially of those coagulation tests which provide only small signals in conventional thromboelastometry (such as test where the blood sample is treated with substances which deactivate the thrombocytes to enable the measurement of the fibrin contribution to the clot firmness solely as mentioned above), or just to decrease the amount of blood which is needed for the test.

The last point is of paramount importance in pharmacology because it would allow repeatable experiments with the blood of a single small laboratory animal such as a mouse. So far there are only two ways to overcome the problem of collecting enough mouse blood for thromboelastography: Pooling of small blood samples (50-100 µl) of several individuals or taking nearly the entire amount of blood of a single individual. The first approach has the disadvantage of averaging out the individual response of each mouse and therefore provides a result that only represents the average values of a multitude of samples. Under these conditions those results which occur only rarely (e.g. one pathological case in a sample consisting of the blood of 10 or more individuals) might not be detectable. The second approach of taking 300 µl would surely be lethal to small animals like mice or the same. This makes it impossible to compare samples taken from the same individual at different points of time, e.g. to monitor the success of a certain treatment or medication with time. Considering the partially high costs for special breeding of laboratory animals also financial considerations make it desirable reduce the amount of animals needed. Furthermore, less animals loose their lives in view of ethical aspects.

BRIEF DESCRIPTION OF THE DRAWINGS

Further features and advantages of the present invention will be evident from a description of embodiments with reference to the figures.

In the figures:

FIG. 7b is a schematic top view of the apparatus according to FIG. 7a;

FIG. 8b is a schematic top view of the apparatus according to FIG. 8a;

DETAILED DESCRIPTION OF PREFERRED EMBODIMENTS

In the following, a first preferred embodiment of the present invention is explained referring to FIG. 3. According to the first embodiment of the invention the apparatus for measuring the coagulation characteristics of particularly a blood sample 1 comprises a cup 2 for receiving the blood sample 1. Furthermore, a respective pin 3 is provided being placeable inside the cup 2.

The cup 2 has basically a cylindrical shape and is for example attached to a base in a stationary manner such that the cup 2 is not able to move relative to the base. Contrary to this, the pin 3 is coupled to the base in a rotatable manner, for example by means of a ball bearing or the same. The provision of a ball bearing can eliminate the high susceptibility to shocks, vibrations and other problems of coagulation diagnosis tools by immersing the pin 3 into the blood sample 1 of the cup 2. Hence, the pin 3 is able to rotate relative to the cup 2.

An elastic element, for example a thin metal spring, is coupled to the pin 3 for the rotational/oscillating movement of the pin 3 relative to the cup 2. Preferably, an optical detection system is provided. For example a mirror is attached to a sidewall of the shaft of the pin 3 for reflecting a light beam from a light source towards a photo detector such that the rotational position of the shaft of the pin 3 is detectable with a high precision.

Figure 3:
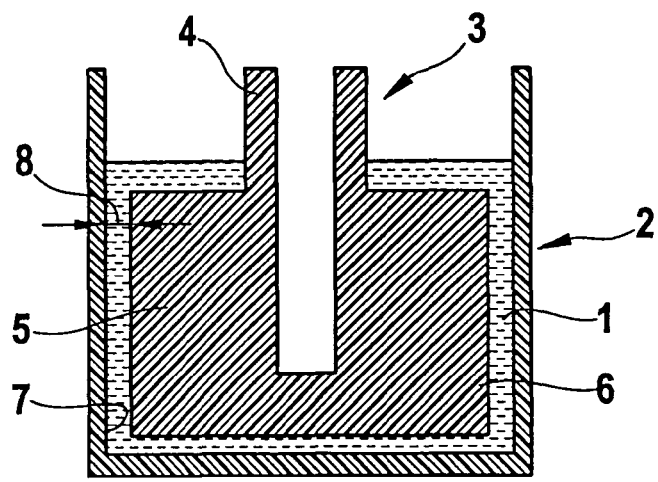
FIG. 3 is a schematic cross-sectional view of an apparatus according to a first preferred embodiment of the present invention.

As can be seen in FIG. 3, the pin 3 according to the first embodiment comprises a shaft 4 and a head portion 5, which according to the first embodiment forms the blood sample contacting portion 6 being immersed into the blood sample 1 in the cup 2 during measurement.

In operation, the cup 2 is stationary and the pin 3 is rotated back and forth by the elastic element in an angular range of about ±5°. When the blood sample 1 begins to clot, it adheres to the surfaces of the contacting portion 6 of the pin 3 and to the surfaces of the cup 2. Hence, the blood clot forms a coupling between the cup 2 and the head portion 5 of the pin 3, whereby a torque acts against the oscillating movement of the pin 3 such that the pin 3 is oscillating in a decreased angular range.

According to the first embodiment of the present invention, the cup 2 comprises a blood sample accommodating portion 7 and the pin 3 comprises the blood sample contacting portion 6, as mentioned above, both having basically a cylindrical shape. The outer diameter of the blood sample contacting portion 6 has to be smaller than the inner diameter of the blood sample accommodating portion 7 of the cup 2 such that the blood sample contacting portion 6 is insertable inside the blood sample accommodating portion 7 of the cup 2.

Furthermore, the cup 2 and the pin 3 are preferably made of a polymer-material, e.g. PMMA, which does not effect coagulation activation before or after a possible plasma treatment.

Figure 1:
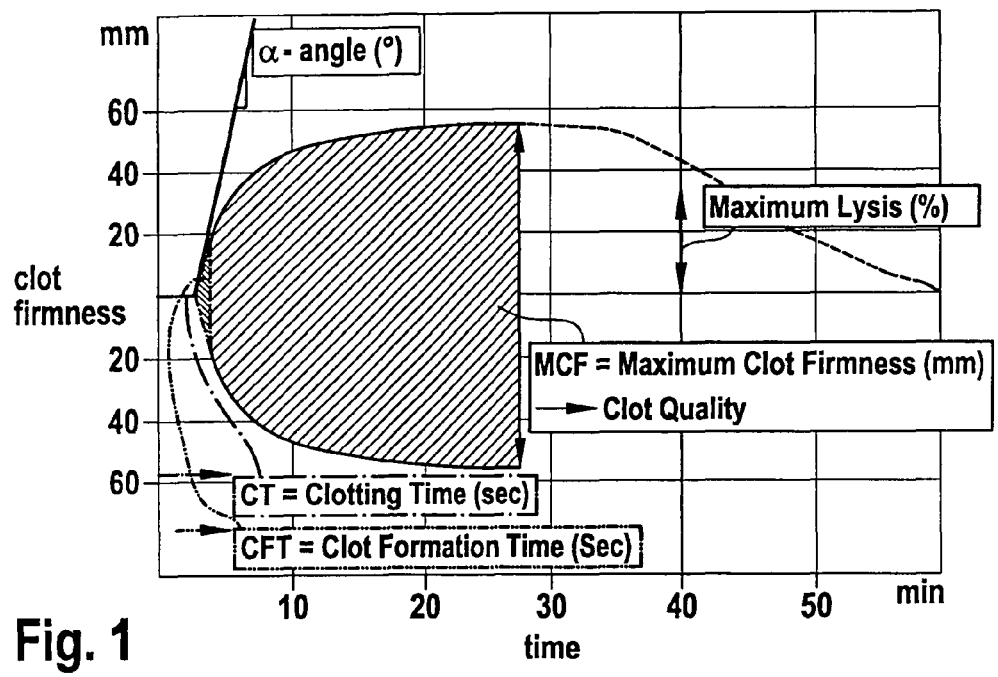
FIG. 1 is an exemplary diagram showing a typical thromboelastometric measurement.
Figure 2:
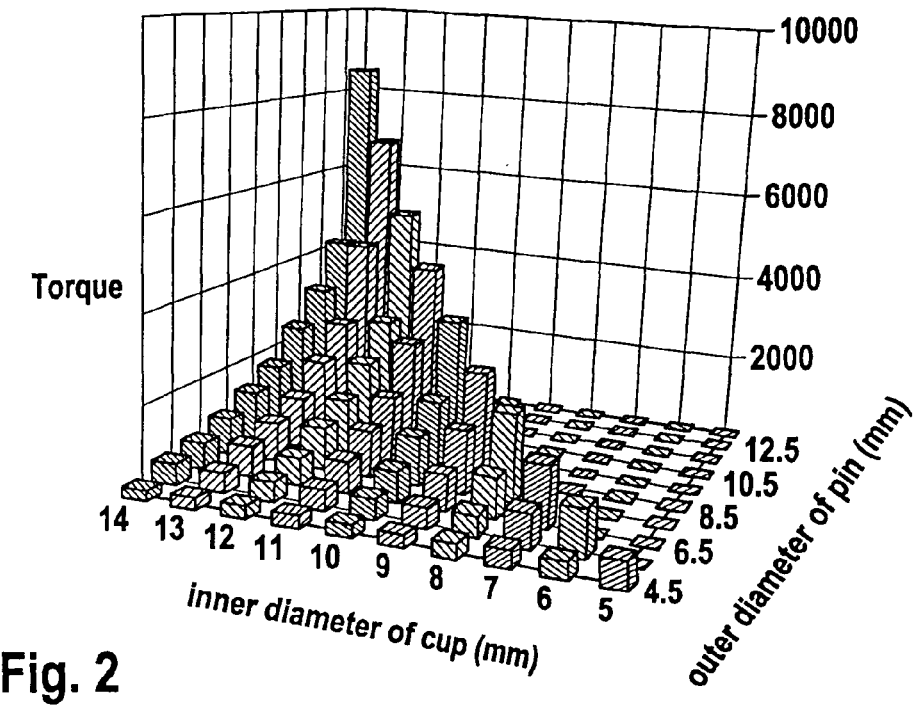
FIG. 2 is a 3-dimensional diagram showing the dependence of the torque on the inner diameter of the cup and the outer diameter of the respective pin.

FIG. 2 illustrates a diagram showing the dependence—discovered by the applicant—of the measured torque on the inner diameter of the blood sample accommodating portion 7 of the cup 2 and on the outer diameter of the blood sample contacting portion 6 of the pin 3. An increased torque increases the measured signal amplitude and provides thus a more sensitive measurement.

It has to be stressed that the dependence of the torque on the inner diameter of the blood sample accommodating portion 7 of the cup 2 and on the outer diameter of the blood sample contacting portion 6 of the pin 3, as found out by the applicant and illustrated in FIG. 2, could not be anticipated from the beginning that easy since complex effects are responsible for this dependence.

As can be seen in FIG. 2, the applicant found out that an increased signal amplitude can be achieved by increasing the inner diameter of the cup 2 and the outer diameter of the pin 3 such that the blood sample gap therebetween remains constant; by decreasing the blood sample gap 8 or by certain combinations of the aforementioned. Hence, it could be found that the signal amplitude can be increased by varying the geometrical dimensions of the cup 2 and the pin 3.

According to the first embodiment illustrated in FIG. 3, the blood sample gap 8 between the opposing surfaces of the pin 3 and the cup 2 has a width in the range of between 0.05 mm and 0.95 mm, and more preferably in the range of between 0.3 mm to 0.7 mm. In particular, the blood sample gap 8 comprises a uniform width along the entire circumference in order to facilitate the uniform blood clot forming along the entire circumference.

Compared to the standardized devices the reduction of the blood sample gap 8 to the above mentioned values results in an increased torque mediated by the elastic blood clot and thus yields in the end higher MCF values. Hence, lower coefficients of variation can be obtained. However, in order to avoid irreversible damages to the fibrin networks it is important to choose a predetermined width of the blood sample gap 8 to provide a mechanically stable fibrin network. Furthermore, the geometrical dimensions of the cup 2 and the pin 3 as well as the width of the blood sample gap 8 have to be chosen such that predetermined parameters do not change that much compared to the standardized devices. For example, the clotting time has to remain within a predetermined range, otherwise no measurement is possible anymore.

As can further be seen in FIG. 2, the torque mediated by the elastic blood clot also increases if the diameter of the cup 2 as well as of the pin 3 are increased while keeping the width of the blood sample gap 8 constant. This also results in higher MCF values. By decreasing the blood sample gap 8 to values below 1 mm, preferably between 0.05 mm and 0.95 mm as mentioned above, the geometry of the apparatus components, i.e. the cup 2 and the pin 3, can be optimized in order to get a maximum elasticity signal per volume blood sample without resulting in irreversible inelastic effects.

By decreasing the width of the blood sample gap 8 to a value between 0.05 mm and 0.95 mm, any test with low signal amplitudes when using conventional cups and pins results now in considerably higher MCF values, e.g. 50 mm or higher for samples from healthy patients and in the range between 10 mm and 30 mm for pathologic samples (constrained: on thromboelastometers calibrated to the Hartert standards).

By increasing the diameters of the cup 2 and the pin 3 higher MCF values can be achieved using the same amount of blood, or same MCF values can be achieved using less amount of blood compared to the cups and pins mentioned as prior art. Preferably, the outer diameter of the blood sample contacting portion 8 of the pin 3 is larger than or equal to 6.0 mm for increasing the ratio between signal amplitude and the needed amount of blood sample 1.

The above described measurement can only be evaluated as long as the fibrin network is sufficiently bound to the surfaces of the blood sample accommodating portion 7 of the cup 2 and to the surfaces of the blood sample contacting portion 6 of the pin 3. If the fibers would tear off even partly, the resulting measurement signal becomes hard to interpret because of interference between this effect and the possible pathologic pattern of hyper fibrinolysis. According to a preferred embodiment of the present invention, at least the blood sample accommodating portion 7 and the blood sample contacting portion 6 are treated by a special process in order to increase the surface adhesion, for example by using the method described in document EP 1,627,725 A2, which is deemed to be incorporated in this description herewith. The treatment for example is constituted as a plasma treatment for improving the adhesion of the blood clot.

Even if not mentioned explicitly, features of the above described first embodiment of the present invention not again mentioned in the following are also applicable to the further described embodiments, for example the plasma treatment, the material choice, the optical detection system, the oscillating system, the geometric dimensions and so on.

Figure 4:
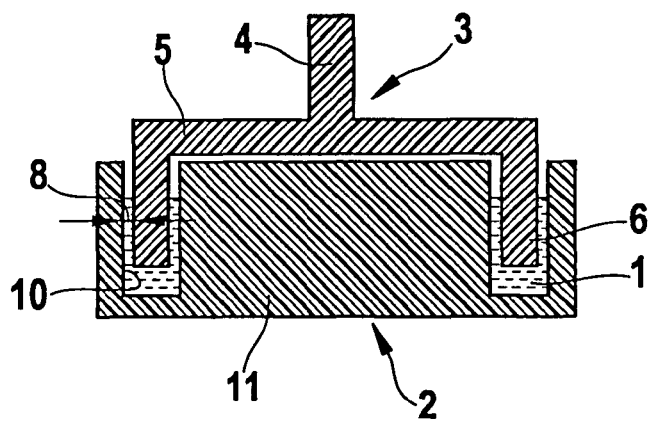
FIG. 4 is a schematic cross-sectional view of an apparatus according to a second preferred embodiment of the present invention.

FIG. 4 shows a schematic cross-sectional view of an apparatus according to a second embodiment of the present invention. For increasing the mediated torque the cup 2 comprises one blood sample duct portion 10 in form of an annular and uniform duct. The blood sample duct portion 10 comprises for example a rectangular cross-section as shown in FIG. 4, a V-shaped cross-section as shown in the third embodiment of FIG. 5, a U-shaped cross-section or any other suitable cross-section.

Figure 5:
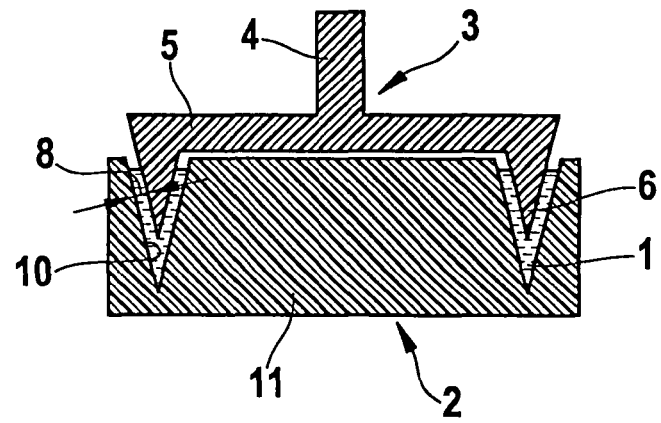
FIG. 5 is a schematic cross-sectional view of an apparatus according to a third preferred embodiment of the present invention.

By leaving a bump 11 in the central area of the axially symmetric cup 2 according to the second and third embodiments of the present invention in regard to FIGS. 4 and 5, the blood sample 1 is accommodated in the blood sample duct portion 10. The bump 11, for example, has a diameter of 0.5 mm or more such that the inner wall of the respective blood sample duct portion 10 has a diameter of 0.5 mm or more and the outer wall of the blood sample duct portion 10 has e.g. a diameter of 1 mm or more. It is obvious for a person skilled in the art that different diameters of the inner wall and the outer wall of the blood sample duct portion 10 are possible such that a predetermined width of the blood sample gap 8 is provided.

A suitable head portion 5 of the pin 3 is provided comprising an annular blood sample contacting portion 6 being insertable inside the blood sample duct portion 10 for forming a blood sample gap 8 having a predetermined width in the range of 0.05 mm to 0.95 mm, preferably 0.3 to 0.7 mm and more preferably of about 0.5 mm. The blood sample contacting portion 6 of the pin 3 comprises approximately the form of a hollow cylinder, wherein the annular cylinder wall is constituting the blood sample contacting portion 6 for being immersed into the blood sample 1, as illustrated in FIGS. 4 and 5.

Thus, it is assured that the blood sample exclusively fills the blood sample duct portion 10 in a predetermined distance from the apparatus axis, whereby the oscillating movement of the cup 2 versus the pin 3 provides in this distance a high contribution to the overall torque and increases the signal amplitude while keeping the required amount of blood sample low.

Additionally, the mediated torque is about twice as high compared to the first embodiment described in FIG. 3, since the number of actively contributing surfaces has been doubled.

Preferably, the geometrical dimension of the blood sample duct portion 10 is formed in a shape that a standard pipette tip can easily be inserted in the duct portion 10. Thus, the mixing steps of the blood sample with the added chemicals is simplified. The mixing step usually consists of drawing the whole amount of liquid into a standard disposable pipette before dispensing it into the cup 2 again and therefore requires that the pipette tip can be positioned just above the bottom of the cup 2. For example, the width of the blood sample duct portion 10 is selected accordingly or the cross-sectional shape of the blood sample duct portion 10 is adapted to the shape of the pipette tip, for example with a V-shaped cross section as illustrated in FIG. 5.

Figure 6:
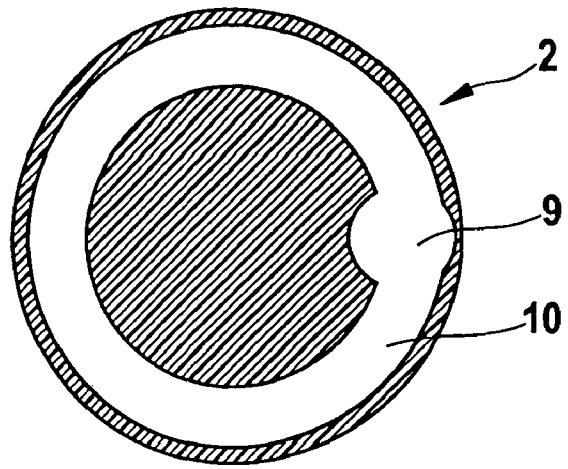
FIG. 6 is a schematic top view of a cup according to a fourth preferred embodiment of the present invention.

Additionally, it is possible to provide the blood sample duct portion 10 with a special pipette tip inserting portion 9, as shown in FIG. 6 illustrating a fourth preferred embodiment of the present invention. The pipette tip inserting portion 9 can be formed as an expanded portion with geometrical dimensions such that the pipette tip can easily be inserted up to the bottom of the blood sample duct portion 10 for facilitating a complete intake of the blood sample 1.

Figure 7A:
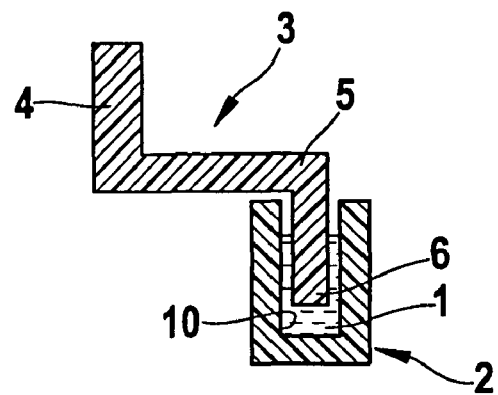
FIG. 7a is a schematic cross-sectional view of an apparatus according to a fifth preferred embodiment of the present invention.
Figure 7B:
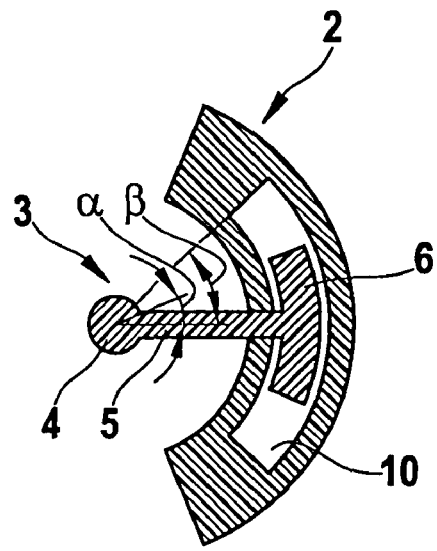

According to a fifth preferred embodiment of the present invention it is referred to FIGS. 7a and 7b, illustrating a schematic cross-sectional view and a schematic top view of the preferred apparatus.

According to the fifth embodiment, the cup 2 comprises one blood sample duct portion 10 as the blood sample accommodating portion being spaced apart from the apparatus axis of preferably about 6.0 mm or more and being extended along a first angular range of 2β in form of a ring segment portion, as illustrated in FIG. 7b. Nevertheless, it is obvious that the distance of the blood sample duct portion 10 from the apparatus axis can be varied arbitrarily in predetermined range in order to achieve increased signal amplitudes. Accordingly, the head portion 5 of the pin 3 comprises an associated blood sample contacting portion 6 in form of a ring segment portion suitable for being inserted in the blood sample duct portion 10 of the cup 2 and extending along a second angular range of 2α, wherein the selected angle α is smaller than the angle β such that an oscillating movement of the test liquid contacting portion 6 of the pin 3 inside the blood sample duct portion 10 of the cup 2 is possible without any interferences. Preferably, the angular range for the oscillating movement is approximately ±5° (i.e. β−α is larger than 5°), wherein for example, β is about 45° and α is about 22.5°. The width of the blood sample duct portion 10 of the cup 2, characterized by the angle β, depends on the selected angle α as well as the angle of the oscillating movement at ideal conditions, for example ±5° as mentioned above. Any other suitable angular ranges are possible as well.

Figure 8A:
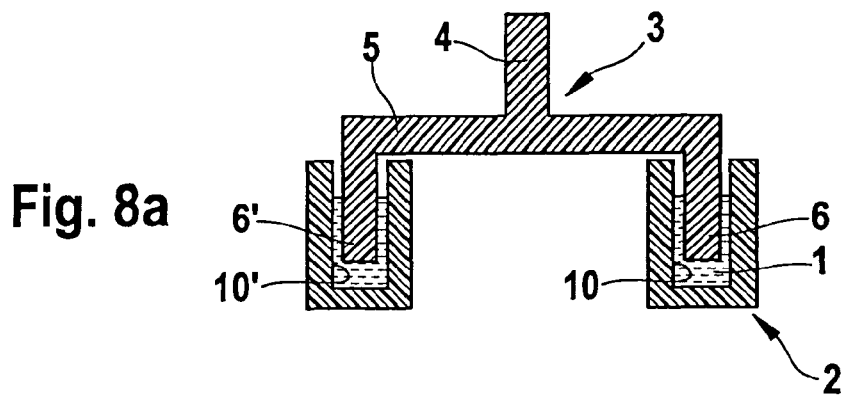
FIG. 8a is a schematic cross-sectional view of an apparatus according to a sixth preferred embodiment of the present invention.
Figure 8B:
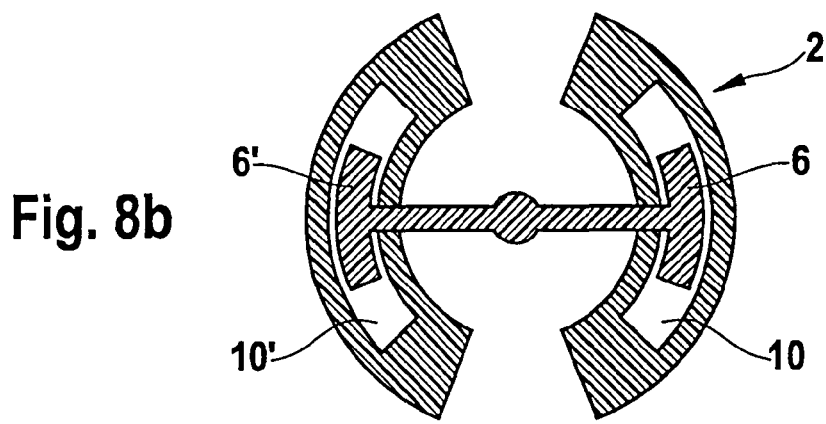

It is apparent for a person skilled in the art that the embodiment described referring to FIGS. 7a and 7b can also be realized by providing the cup with two or more blood sample duct portions 10, 10' in form of a ring segment portion and accordingly by providing the pin 3 with a respective number of test liquid contacting portions 6, 6' in form of a ring segment portion each being placeable inside the associate blood sample duct portion 10, 10' of the cup 2, as illustrated in FIGS. 8a and 8b as a sixth embodiment of the present invention.

In particular, the blood sample duct portions 10, 10' are advantageously arranged in a symmetrical manner and provided with identical symmetrical dimensions to minimize any contribution to overall torque which can result in a tilting of the axis of the apparatus.

Furthermore, the single blood sample duct portions 10, 10' of the cup 2 can be connected via suitable blood sample channels in order to facilitate the introduction of the blood sample 1 into the single blood sample duct portions 10, 10' of the cup 2.

It is obvious for a person skilled in the art that an arbitrary cross-sectional shape of the blood sample accommodating portion, i.e. the blood sample duct portions 10, 10', of the cup 2 and the respective blood sample contacting portions 6, 6' of the pin 3 is possible as well as an arbitrary number of accommodating portion/contacting portion pairs. It is even possible that one pair comprises a first predetermined geometrical dimension and cross-sectional shape and another pair comprises a second deferring geometrical dimension and cross-sectional shape. It is merely recommended that the shape of the contacting portion of the pin and the accommodating portion of the cup are adapted to each other such that the corresponding side walls of the accommodating portion of the cup and lateral surfaces of the contacting portion of the pin are parallel to each other under working conditions, forming a blood sample gap having preferably a uniform width. This is just optional and it is possible that the width of the gap varies along its circumferential extension. Furthermore, neither the cup nor the pin has to be exactly axially symmetric. Deviations from axial symmetry are tolerable as long as the oscillating movement of the pin relative to the cup is not hindered in any way.

A possible tilting of the axis which might occur due to the unsymmetrical construction of the apparatus can be addressed by increasing the number of blood sample accommodating portions in the cup and the respective number of blood sample contacting portions of the pin and arranging all of them in a symmetrical manner. Alternatively, the suspension of the axis could be modified in order to make it less susceptible to tilting.

Figure 9:
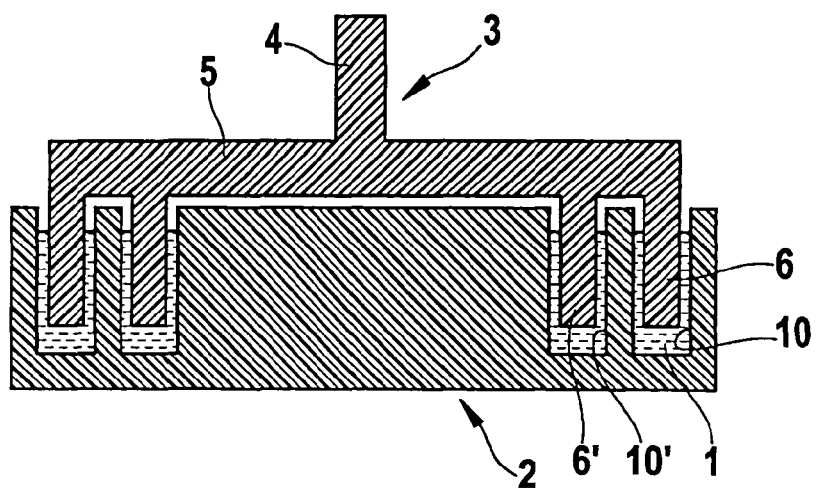
FIG. 9 is a schematic cross-sectional view of an apparatus according to a seventh preferred embodiment of the present invention.

FIG. 9 illustrates a seventh preferred embodiment of the present invention. According to this embodiment, the cup 2 comprises four blood sample duct portions, two blood sample duct portions 10, 10' on each opposing side being radially spaced apart, as viewed in a cross-sectional view in FIG. 9. Hence, according to the present embodiment four Blood sample accommodating portions are provided inside the cup 2 for increasing the number of actively contributing surfaces. Accordingly, the pin 3 comprises a respective number of suitable blood sample contacting portions 6, 6', as also illustrated in FIG. 9.

Figure 10:
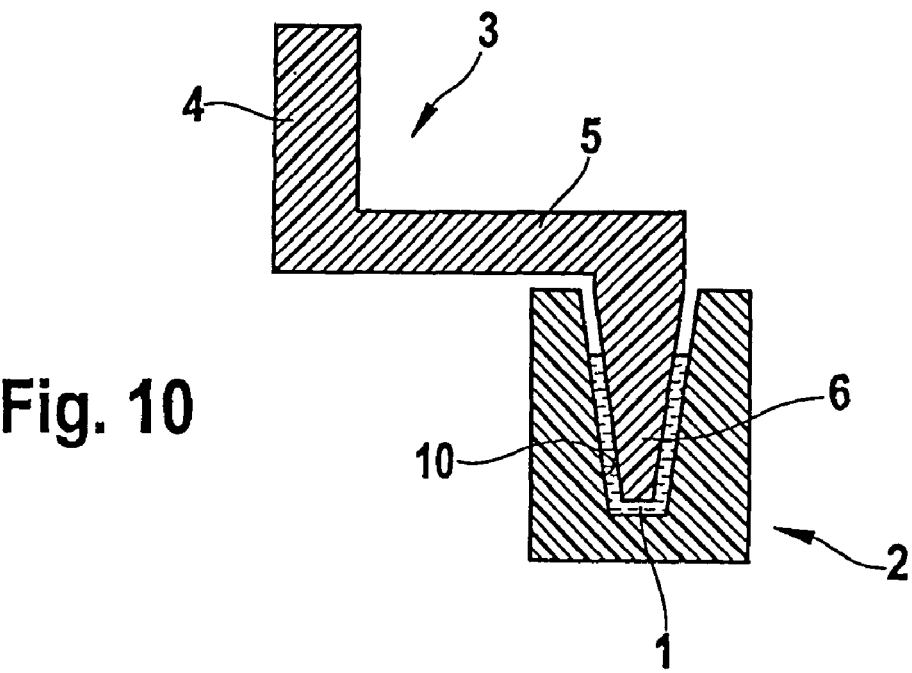
FIG. 10 is a schematic cross-sectional view of an apparatus according to an eighth preferred embodiment of the present invention.
Figure 11:
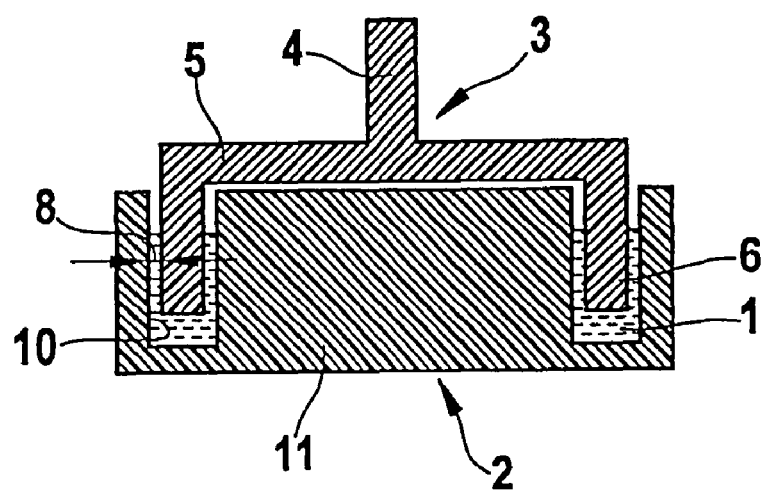
FIG. 11 is a schematic cross-sectional view of the apparatus according to a preferred embodiment of the present invention.

The cross-section of each pair consisting of a blood sample duct portion and a blood sample contacting portion could be varied such that the cross-section is for example V-shaped (see sample contacting portion of FIG. 10), U-shaped, rectangular shaped or the same.

By suitable geometrical dimensions of the cup and the pin one can achieve that tests of normal samples result in MCF-values of 50 mm or slightly above, while pathologic samples exhibiting low fibrin concentrations lay between 10 mm and 30 mm. Nevertheless, the usage of a different set of cups and pins comprising different geometrical dimensions, which provides different results on the same type of measurements, could cause confusion in some cases. Therefore, the apparatus preferably comprises an analysis software which is programmed to treat the raw data collected by using disposable cups and pins according to for example the above mentioned embodiments in such a way that the displayed parameters (MCF, CFT . . . ) equal those achieved under the usage of conventional cups and pins. The measured raw data, i.e. the deflection of the pin versus the cup (which is proportional to the position of the reflected light beam for example in the ROTEM device described in the introductory portion of the description), which are used by the suitable software to calculate the parameters which in turn are displayed to the operator (such as MCF, CFT, CT . . . ) strongly depend on the geometrical dimensions of the cup and the pin used. The analysis software for analyzing and presentation of thromboelastography data is preferably programmed in such a way, that one or more conversion factors are chosen on which type of cup and pin is used for the present measurement. The software is therefore modified such that the signals recorded by using cups and pins with the above described new geometrical dimensions are treated by different modules to calculate the displayed parameters. Hence, it can be achieved that two identical tests performed under the use of different cups and pins always result in identical parameters (MCF, CFT, CT . . . ) being displayed to the user. Thus, the accuracy of the measurements would profit from the adapted cup and pin geometry and the user is able to interpret the single measurement result without taking the different geometrical dimensions into consideration. This enhances the comparability of measurements obtained by means of standardized systems and systems according to the present invention. Thus, the acceptance of an apparatus comprising geometrical dimensions of the cups and the pins of the present invention is increased.

According to the present invention, a new design for the cups and pins is invented which uses the effect of higher signals when reducing the gap between the cup and the pin. The new design requires that inelastic effects—which can occur if the sample is stretched too much—can be excluded. An experimental limit of 0.05 mm gap width for the minimum gap could be found, thus defining the limitations of the new design.

Although the present invention has been described in accordance with preferred embodiments, it is obvious for a person skilled in the art that modifications are possible in all embodiments. For example, the cross-sectional shapes of the respective blood sample contacting portions and blood sample accommodating portions can be varied arbitrarily in accordance with each other. Furthermore, the number of respective contacting portion/accommodation pairs can be varied in all embodiments as well. Additionally, the position of the contacting portion/accommodating portion pairs relative to each other can be modified as well arbitrarily. All the above-mentioned features of the single embodiments can be combined advantageously as long as the chosen geometrical dimensions of the contacting portion/accommodating portion pairs are suitable to provide increased signal amplitudes compared to the devices according to the prior art.

REFERENCE SIGNS 1 blood sample
2 cup
3 pin
4 shaft
5 head portion
6 blood sample contacting portion
6' blood sample contacting portion
7 blood ample accommodating portion
8 blood sample gap
9 pipette tip inserting portion
10 test liquid duct portion
10' test liquid duct portion
11 bump
2β first angular range
2α second angular range

The invention claimed is:

1. Apparatus for measuring coagulation characteristics of a test liquid, in particular of a blood sample, comprising:
   a cup for receiving said test liquid;
   a pin having a head portion suitable to be immersed into said test liquid of said cup;
   wherein said cup comprises at least one test liquid duct portion;
   wherein said head portion of said pin comprises at least one test liquid contacting portion, wherein each test liquid contacting portion is associated to and placeable inside the respective test liquid duct portion of said cup such that the lateral surfaces of the respective test liquid contacting portion of said pin and side walls of the associated test liquid duct portion of said cup are forming a test liquid gap there between having a predetermined width; and
   wherein said at least one test liquid duct portion and said associated test liquid contacting portion are shaped as a ring-segment.

2. Apparatus according to claim 1, wherein said test liquid gap has a width in a range of about 0.05 mm to 0.95 mm.

3. Apparatus according to claim 2, wherein said test liquid gap has a width in a range of about 0.3 mm to 0.7 mm.

4. Apparatus according to claim 3, wherein said test liquid gap has a width in a range of about 0.5 mm.

5. Apparatus according to claim 1, wherein said test liquid gap comprises a uniform width.

6. Apparatus according to claim 1, wherein said at least one test liquid duct portion and said at least one test liquid contacting portion comprise an axially symmetrical shape, respectively.

7. Apparatus according to claim 6, wherein said at least one test liquid duct portion is shaped as an annular duct and said associated test liquid contacting portion is shaped as an annular contacting portion accordingly.

8. Apparatus according to claim 1, wherein said cup comprises one test liquid duct portion and said pin comprises one associate test liquid contacting portion.

9. Apparatus according to claim 1, wherein said cup comprises two or more test liquid duct portions in symmetrical manner and said pin comprises a respective number of test liquid contacting portions each being associated to one of said test liquid duct portions, respectively.

10. Apparatus according to claim 9, wherein said two or more test liquid duct portions are fluidly connected via respective connecting channels being provided inside of said cup for simplifying a pipetting process.

11. Apparatus according to claim 1, wherein each test liquid duct portion extends along a predetermined first angular range (2β) and each associated test liquid contacting portion extends along a predetermined second angular range (2α), wherein said first angular range (2β) is larger than said second angular range (2α) to enable an undisturbed oscillating movement of each test liquid contacting portion inside the associated test liquid duct portion.

12. Apparatus according to claim 1, wherein said at least one test liquid duct portion and said associated test liquid contacting portion comprise a rectangular, V-shaped, U-shaped cross-section.

13. Apparatus according to claim 1, wherein said at least one test liquid duct portion comprises a local expanded pipette tip inserting portion for an easy insertion of a corresponding pipette tip.

14. Apparatus according to claim 1, wherein said cup and said pin comprise a polymer material being treatable with a surface adhesion increasing treatment, for example a plasma treatment, for increasing the test liquid adhesion to the relevant surfaces of said cup and said pin.

15. Apparatus according to claim 1, wherein said cup is attached to a base in a stationary manner and said pin is coupled to said base via a bearing, for example a ball bearing, in a rotatable manner.

16. Apparatus according claim 1, wherein said apparatus comprises a system for oscillating said cup and said pin relative to each other having an elastic element, for example a fine metal spring, for providing restoring forces for said oscillating movement.

17. Apparatus according to claim 1, wherein said apparatus comprises a system for measuring an oscillating movement of said cup and of said pin relative to each other for determining coagulation characteristics of said test liquid having an optical detection system, for example a mirror being attached to said pin for reflecting a light beam of a corresponding light source, for detecting a rotational position of said pin.

18. Method for measuring the coagulation characteristics of a test liquid, in particular of a blood sample, via an apparatus according to claim 1, comprising:
   (a) measuring scillation movement signal values by using said cup and said pin having predetermined geometrical dimensions; and
   (b) determining the coagulation characteristics of the test liquid using said signal values.

19. A non-transient computer-readable medium containing code for executing the method according to claim 18.

* * * * *

UNITED STATES PATENT AND TRADEMARK OFFICE
CERTIFICATE OF CORRECTION

PATENT NO.         : 8,322,195 B2                         Page 1 of 1
APPLICATION NO.    : 12/520034
DATED              : December 4, 2012
INVENTOR(S)        : Glauner et al.

It is certified that error appears in the above-identified patent and that said Letters Patent is hereby corrected as shown below:

Please correct claim 18, Line 54-61 as follows:

Method for measuring the coagulation characteristics of a test liquid, in particular of a blood sample, via an apparatus according to claim 1, comprising:
(a) measuring ~~scillation~~ oscillation movement signal values by using said cup and said pin having predetermined geometrical dimensions; and
(b) determining the coagulation characteristics of the test liquid using said signal values.

Signed and Sealed this
Fifth Day of March, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,322,195 B2
APPLICATION NO. : 12/520034
DATED : December 4, 2012
INVENTOR(S) : Glauner et al.

It is certified that error appears in the above-identified patent and that said Letters Patent is hereby corrected as shown below:

IN THE CLAIMS

Please correct claim 18, column 12, lines 54-61 as follows:

Method for measuring the coagulation characteristics of a test liquid, in particular of a blood sample, via an apparatus according to claim 1, comprising:
(a) measuring ~~scillation~~ oscillation movement signal values by using said cup and said pin having predetermined geometrical dimensions; and
(b) determining the coagulation characteristics of the test liquid using said signal values.

This certificate supersedes the Certificate of Correction issued March 5, 2013.

Signed and Sealed this
Ninth Day of April, 2013

Teresa Stanek Rea
*Acting Director of the United States Patent and Trademark Office*